(12) United States Patent
Linder et al.

(10) Patent No.: US 8,263,409 B2
(45) Date of Patent: Sep. 11, 2012

(54) METHOD AND APPARATUS FOR ESTIMATING A MECHANICAL PROPERTY

(75) Inventors: Sten Linder, Trosa (SE); Lennart Thegel, Västerås (SE)

(73) Assignee: ABB AB, Västerås (SE)

( * ) Notice: Subject to any disclaimer, the term of this patent is extended or adjusted under 35 U.S.C. 154(b) by 580 days.

(21) Appl. No.: 12/084,973

(22) PCT Filed: Oct. 31, 2006

(86) PCT No.: PCT/SE2006/050444
§ 371 (c)(1),
(2), (4) Date: Sep. 4, 2009

(87) PCT Pub. No.: WO2007/055649
PCT Pub. Date: May 18, 2007

(65) Prior Publication Data
US 2009/0315572 A1    Dec. 24, 2009

Related U.S. Application Data

(60) Provisional application No. 60/737,378, filed on Nov. 17, 2005.

(30) Foreign Application Priority Data

Nov. 14, 2005 (SE) .................................. 0502505

(51) Int. Cl.
*G01R 27/08* (2006.01)
(52) U.S. Cl. .................... 436/73; 422/82.01; 422/82.02; 324/693
(58) Field of Classification Search .................... 436/73; 422/82.01, 82.02; 324/693, 207.17, 716, 324/717
See application file for complete search history.

(56) References Cited

U.S. PATENT DOCUMENTS

| 3,628,137 A | * | 12/1971 | Mazur ........................... 324/717 |
|---|---|---|---|
| 4,428,782 A | | 1/1984 | Walker et al. |
| 4,947,117 A | | 8/1990 | Buck et al. |
| 5,059,902 A | | 10/1991 | Linder |
| 5,811,970 A | | 9/1998 | Cook et al. |

(Continued)

FOREIGN PATENT DOCUMENTS

JP    2002-031613 A    1/2002

(Continued)

OTHER PUBLICATIONS

International Search Report, dated Mar. 2, 2007, issued in connection with counterpart International Application No. PCT/SE2006/050444.

(Continued)

*Primary Examiner* — Vickie Kim
*Assistant Examiner* — Dwan A Gerido
(74) *Attorney, Agent, or Firm* — Venable LLP; Eric J. Franklin (57) ABSTRACT

An apparatus for estimating or supervising one or more internal mechanical properties of a metal alloy object with a known chemical composition based on the resistivity of the metal alloy object. The apparatus includes a device for measuring the resistivity of the metal alloy object, and a computation unit adapted to calculate the content of dissolved alloying elements in the metal alloy object based on the measured resistivity and the known chemical composition of the metal alloy, and based thereon to calculate at least one internal mechanical property of the metal alloy object.

31 Claims, 3 Drawing Sheets

U.S. PATENT DOCUMENTS 5,977,766 A * 11/1999 Linder et al. .................. 324/225

FOREIGN PATENT DOCUMENTS

JP            2002-236119 A        8/2002

OTHER PUBLICATIONS

Written Opinion of the International Searching Authority, dated Mar. 2, 2007, issued in connection with counterpart International Application No. PCT/SE2006/050444.

Notice of Rejection, issued on Jun. 14, 2011 by the Japanese Patent Office in connection with counterpart Japanese Application No. 2008-541121.

Senri Masuda et al., Cu-Fe gokin no kyodo to dodenritsu ni oyobosu Fe ganyuritu no eikyo [Influence of Fe Content on Strength and Conductivity of Cu-Fe Alloy], Collected Abstracts of the Japan Institute of Metals, p. 268, Sep. 28, 2004.

Chan-Joo Kim et al., Variations of Harness Electric Conductivity with Cr and Zr Contents in Cu-Cr-Zr Alloys, J. of the Korean Inst. of Met. & Mater., vol. 33, No. 11, pp. 1399-1405, 1995.

Supplementary European Search Report, dated Apr. 2, 2012, issued in connection with counterpart European Application No. EP 06 81 3064.

Linder, S., "Simultaneous strip thickness and conductivity measurement," *MPT Metallurgical Plant and Technology International*, Verlag Stahleisen, Duesseldorf, DE, vol. 28, No. 3, Jun. 1, 2005, pp. 50-53.

Byeon, Jai Won, et al., "Nondestructive evaluation of thermally degraded 2.25Cr-1Mo steel by electrical resistivity measurement," *Materials Transactions Japan Inst. Metals*, Japan, vol. 44, No. 6, Jun. 2003, pp. 1204-1208.

Fraenkel, W., et al., "Improving aluminum alloys," *Zeit. Fur Metallkunde; Zeitschrift Fur Metallkunde*, Mar. 1922, vol. 14, No. 3.

Simchi, A., et al., "Microstructural changes in Mo steels during sintering and effect on electrical conductivity," *Powder Metallurgy*, vol. 45, No. 4, Dec. 1, 2002, pp. 307-314.

* cited by examiner

METHOD AND APPARATUS FOR ESTIMATING A MECHANICAL PROPERTY

CROSS-REFERENCE TO RELATED APPLICATIONS

This application claims priority to U.S. provisional patent application 60/737,378 filed 17 Nov. 2005 and Swedish patent application 0502505-1 filed 14 Nov. 2005 and is the national phase under 35 U.S.C. §371 of PCT/SE2006/050444 filed 31 Oct. 2006.

FIELD OF THE INVENTION

The present invention relates to an estimation of one or more internal mechanical properties of a metal alloy object with a known chemical composition based on the resistivity of the metal alloy. In particular it relates to estimation of the strength of the metal alloy object. The invention is useful in connection with production of any type of object made of a metal alloy. The production can be continuous, semi-continuous or piece-by-piece. The invention is particularly useful in connection with continuous production of alloy strips, sheets rods, bars and similar products.

PRIOR ART

When it comes to the production of objects made of a metal alloy, there are two important properties that influence the quality of the produced object: the dimensions of the object, such as the thickness of a flat object or the diameter of a round object, and the internal mechanical properties, such as the tensile strength, the yield strength, and the elongation of the metal alloy object. The yield strength of the metal alloy is defined as the maximum force that can be applied to the metal alloy object, before it becomes deformed. The tensile strength is defined as the maximum force that can be applied to the metal alloy object before it breaks. The elongation is defined as the amount of lengthening of the metal alloy object before it breaks, when a pulling force is applied to the object. The tensile strength, the yield strength, and the elongation of the metal alloy reflect the strength of the object. Thus, the internal mechanical properties of an object reflect the quality of the object.

Today it is possible to continuously measure the dimension thickness of a rolled flat metal alloy object, such as a strip or a sheet, in a rolling mill, and to control the thickness of the sheet in dependence on the measured thickness and a desired value of the thickness, in order to improve the accuracy of the accomplished thickness of the sheet. The same is valid for a metal alloy with round or rectangular cross section, as a bar or a rod, regarding the dimension diameter or side.

Today, for controlling the strength of the alloy object, a sample of the object is taken and analyzed off-line by means of laboratory equipment. This method is troublesome and time consuming. Due to end phenomena during casting of the object, the thermal conditions will differ between the ends of the object and the rest of the object. Those differences may affect the strength of the object, in particular for sensitive alloys, such that the strength at the ends will differ from the strength in the rest of the object. A problem in connection with this is that, due to better accessibility, the test samples usually are taken at the ends of the alloy object, which means that the result of the strength analysis may be misleading.

Accordingly, today it is not possible to continuously, during production, in a contactless way measure the strength of a metal alloy object. However, it is a desire to be able to do that, for example in order to be able to control the strength of the alloy object during production thereof.

In the document U.S. Pat. No. 4,947,117 it is stated that the conductivity is directly related to a material's ultimate strength. However, the relation between the conductivity and strength of an object is more complicated than that.

OBJECTS AND SUMMARY OF THE INVENTION

The object of the present invention is therefore to provide an attractive and general solution, which alleviates the problems above, and thus makes it possible to estimate and/or supervise the internal mechanical properties of a metal alloy object during production thereof, without interfering with the production.

According to one aspect of the invention, this object is achieved with a method. The method comprises determining the resistivity of the metal alloy object, calculating the content of dissolved alloying elements in the metal alloy based on the measured resistivity and the known chemical composition of the metal alloy, and based thereon calculating at least one internal mechanical property of the metal alloy.

Since conductivity is the inverted resistivity, it is to be understood that the conductivity could be used as well as the resistivity to calculate the internal mechanical properties of the metal alloy. The resistivity, or the conductivity, of the object is measured. Determining the resistivity also includes the possibility to measure the conductivity and use the conductivity to calculate the internal mechanical properties of the metal alloy.

A metal alloy includes a main phase where a main metal component is dominating and one or more alloying elements are dissolved. The main component is for instance aluminum, iron or copper. The alloying elements are in lower content than the main component and are, for instance one or more of the following substances, iron, chromium, nickel, manganese, magnesium and zinc. A metal alloy further often also includes phases not dissolved in the main component, but precipitated as separate phases. Those precipitated phases are characterized as intermetallic phases if they have metallic character and can contain the main component and the alloying elements.

By dissolved alloying elements in the metal alloy is meant the alloying elements dissolved in the main phase. The content of dissolved alloying elements in the metal alloy object is, for example, calculated as percentage by volume, percentage by weight, or atomic percentage in relation to the whole alloy object. Alternatively, the content of dissolved alloying elements in the metal alloy could be calculated as percentage in relation to the main phase. The content of dissolved alloying element in the alloy is calculated for each alloying element, and the internal mechanical property of the metal alloy is determined based on the content of dissolved alloying element for each of the alloying elements.

The relation between the amounts of alloying elements dissolved in the main component and as precipitated intermetallic phase affects the internal mechanical properties of the metal alloy. The invention uses the fact that the internal mechanical properties of the metal alloy depend on the content of dissolved alloying elements in the metal alloy and the chemical composition of the metal alloy. Since the content of dissolved alloying elements in the metal alloy depends on the content of precipitated alloying elements in the alloy and the total amount of alloying elements in the alloy, it is possible to use the content of precipitated alloying elements in the alloy for calculating the content of dissolved alloying elements in the alloy. Thus, when in this application it is referred to the content of dissolved alloying elements, it is to be understood that the content of precipitated alloying elements could be used as well, if an adjustment of the calculation is made.

A prerequisite for the method according to the invention is that the chemical composition of the metal alloy object, i.e. the amount of alloying substances in the metal alloy, is known beforehand. Normally, this is known by a chemical analysis of the metal alloy object.

The invention makes it possible to estimate the internal mechanical properties of a metal alloy object based on a measured resistivity or conductivity. It is no longer necessary to rely on laboratory tests on removed samples from the object. The method according to the invention is fast and easy to use. The invention makes it possible to immediately provide an operator of a production process with information of the internal mechanical properties of the produced object and thereby of the quality of the object. As the operator receives information about the quality of the object during production of the object, it is possible for the operator to control the further processing of the object so that a desired quality of the object is achieved. Another advantage with the method according to the invention is that it is possible to check the quality of the entire object, and not just a sample test.

According to an embodiment of the invention, the resistivity of the alloy object is continuously, or at least repeatedly, measured during production of the object, and the internal mechanical property of the object is repeatedly calculated based thereon. This embodiment makes it possible to continuously supervise and/or control the quality of the produced objects. The continuous estimation of the internal mechanical properties is a prerequisite for control of the quality.

According to an embodiment of the invention, the metal alloy object undergoes a certain degree of thickness reduction during production of the object, and the internal mechanical property of the metal alloy object is calculated based on the degree of reduction. During production of some alloy objects, the objects pass through a process step that reduces the thickness of the object, for example rolling of the object. The internal mechanical properties of an alloy object depend on the degree of thickness reduction, which the object has gone through during production thereof. In this embodiment, the internal mechanical properties are calculated with regard to the thickness reduction of the object. Thereby, the estimation of the internal mechanical property is improved.

According to an embodiment of the invention, the method comprises: receiving the temperature of the metal alloy object, calculating the resistivity at a given reference temperature based on the temperature of the object and the measured resistivity, and calculating the content of dissolved alloying elements in the metal alloy based on the resistivity at the reference temperature. Preferably, the reference temperature is close to room temperature. For example, the reference temperature is in the interval of 15-30° C. The resistivity depends strongly on the temperature of the measured object. According to this embodiment, the measured resistivity is recalculated to the resistivity at a given reference temperature, before it is used in further calculations. Thereby, the temperature dependence of the resistivity is removed and the estimation of the internal mechanical property is improved.

According to an embodiment of the invention, the content of dissolved alloying elements in the metal alloy object is calculated by means of thermodynamic calculations. These calculations are carried out to achieve possible content of dissolved alloy elements depending upon a variable equilibrium temperature. Thus, using thermodynamic calculations makes it possible to express the content of a multitude of dissolved alloy components with only one parameter, the equilibrium temperature. It is also convenient to use thermodynamic calculations to calculate the content of dissolved alloying elements in the alloy object, since commercially available computing programs can be used to carry out the calculations.

According to an embodiment of the invention, the content of dissolved alloying elements in the metal alloy is calculated based on a first mathematical relationship between the resistivity in the metal alloy, the content of dissolved alloying elements in the metal alloy, and the known chemical composition of the metal alloy, and a second mathematical relationship between the content of a dissolved alloying element in the metal alloy, the known chemical composition of the metal alloy, and an equilibrium temperature. The equilibrium temperature is iteratively calculated based on the first and second mathematical relationships, and the content of dissolved alloying elements in the metal alloy is calculated based on the calculated equilibrium temperature and the second mathematical relationship.

According to an embodiment of the invention, the calculated internal mechanical property reflects the strength of the metal alloy object. Mechanical properties that reflect the strength of the metal alloy object are, for example, the tensile strength, the yield strength, and the elongation of the object. The desired internal strength property is calculated based on the calculated content of dissolved alloying elements in the metal alloy, and the internal strength property of the main component of the alloy, for example, the tensile strength of the main component, or the yield strength of the main component. The tensile strength and the yield strength of the main component are known, for example, from published tables.

According to an embodiment of the invention, the resistivity of the metal alloy object is measured by means of a contactless measuring method. For example, the resistivity is measured by a technology using Pulsed Eddy Currents (PEC). The contactless measuring makes it possible to estimate the internal mechanical properties of an object in motion, such as a moving strip, bar, wire or similar in a rolling mill or any other continuous metal working process. The object in motion could also be a wire, rod or a tube in a drawing process.

According to an embodiment of the invention, the method further comprises calculating the content of precipitated alloying elements in the metal alloy object, and based thereon calculating at least one internal mechanical property of the metal alloy object. For example, the content of precipitated alloying elements is calculated as the difference between the known content of metal alloying elements in the alloy object and the calculated content of dissolved alloying elements in the alloy object. Often the mechanical properties of the alloy object are determined only by the conditions in the main phase, but in some cases also the precipitated phases affects the mechanical properties. In these cases also the amount of precipitated phases should be determined. This embodiment also considers the influence on the internal mechanical properties arising from precipitated alloying elements in the alloy. Thus, the accuracy of the estimation of the mechanical properties is improved.

According to an embodiment of the invention, the method comprises: calculating the content of dissolved and/or precipitated alloy elements and based thereon calculating at least one internal mechanical property of a specific metal alloy, in a calibration step comparing the calculated value for a specific sample with a measured value of the internal mechanical property on the same sample in a mechanical test, and adjusting the calculated values in accordance to the measured value.

A calculated and a measured mechanical value of the same specific sample are used to provide a calibration factor. The adjustment could either be done by multiplying the calculated values by the calibration factor or by adding the calibration factor to the calculated values. Thus, a calibration factor, calculated based on a calculated and a measured value of the same specific sample, is used in order to calibrate the estimation of the mechanical properties and thereby to improve future estimations.

According to an embodiment of the invention, the method further comprises supervising the quality of the produced object based on the calculated internal mechanical property of the object. This embodiment is particularly useful for supervising the quality of a moving alloy object, such as an aluminum alloy sheet or strip, during production of the object. This embodiment makes it possible to supervise the quality of an object during production thereof, and accordingly take measures if the quality is not satisfactory, thereby improving the quality of the produced object.

According to an embodiment of the invention, the internal mechanical property of the object is continuously, or at least repeatedly, calculated during production of the object, and the method further comprises: continuously or at least repeatedly adjusting the production process in accordance with the estimated property of the object in order to improve the quality of the produced object. This embodiment makes it possible to continuously control a production process for producing metal alloy objects with regard to an estimated internal mechanical property of the produced object, and thereby improve the quality of the produced object.

According to an embodiment of the invention, the internal mechanical property of the object is continuously or at least repeatedly calculated during production of the object, and the method further comprises: calculating a degree of heating of the alloy object based on the calculated mechanical property, and heat treating the alloy object in accordance with the calculated degree of heating. The degree of heating is, for example, the temperature and time of the heat treatment. This embodiment makes it possible to determine an optimized degree of heat treatment for an individual object, or part of the object, during production of the object, in order to improve the quality of the produced object.

It is easy to realize that the method according to the invention is suitable for execution by a computer program having instructions corresponding to the steps in the inventive method when run on a processor unit.

According to a further aspect of the invention, the object is achieved by a computer program directly loadable into the internal memory of a computer or a processor, comprising software code portions for performing the steps of the method when the program is run on a computer. The computer program is provided either on a computer-readable medium or through a network.

According to another aspect of the invention, the object is achieved by a computer readable medium having a program recorded thereon, when the program is to make a computer perform the steps of the method and the program is run on the computer.

According to another aspect of the invention, this object is achieved by an apparatus.

Such an apparatus comprises a device for measuring the resistivity of the metal alloy object, and computation unit adapted to calculate the content of dissolved alloying elements in the metal alloy object based on the measured resistivity and the known chemical composition of the metal alloy, and based thereon to calculate at least one internal mechanical property of the metal alloy object. The device for measuring the resistivity of the metal alloy object could as well measure the conductivity of the metal alloy object and use the measured conductivity to calculate the internal mechanical properties of the metal alloy.

According to another aspect of the invention, this object is achieved by a method for supervising a process for producing a metal alloy object with a known chemical composition.

This method comprises determining the resistivity of the metal alloy object, estimating the content of dissolved alloying elements in the metal alloy object based on the determined resistivity and the chemical composition of the metal alloy object, estimating the content of precipitated alloying elements in the metal alloy object based on the determined resistivity and the chemical composition of the metal alloy object, and supervising the production process based on the ratio between the estimated content of dissolved alloying elements and the estimated content of precipitated alloying elements. As the ratio between the contents of dissolved alloying elements and precipitated alloying elements reflects the internal mechanical properties of the metal alloy, it is possible to supervise the production process based on fluctuations in the ratio between the contents of dissolved and precipitated alloying elements in the produced object. For example, the supervision can be done automatically by means of a computer program, and an operator is notified upon detection of fluctuations in the ratio between the contents of dissolved and precipitated alloying elements.

According to an embodiment of the invention, the estimated contents of dissolved and precipitated alloying elements in the metal alloy object are presented to the operator. It is convenient for the operator if the ratio between the estimated content of dissolved and precipitated alloying elements is calculated and presented to the operator. Thereby, it is possible for the operator to notice changes in the ratio and thus to detect if something is wrong with the process.

BRIEF DESCRIPTION OF THE DRAWINGS

The invention will now be explained more closely by the description of different embodiments of the invention and with reference to the appended figures.

DETAILED DESCRIPTION OF PREFERRED EMBODIMENTS OF THE INVENTION

Figure 1:
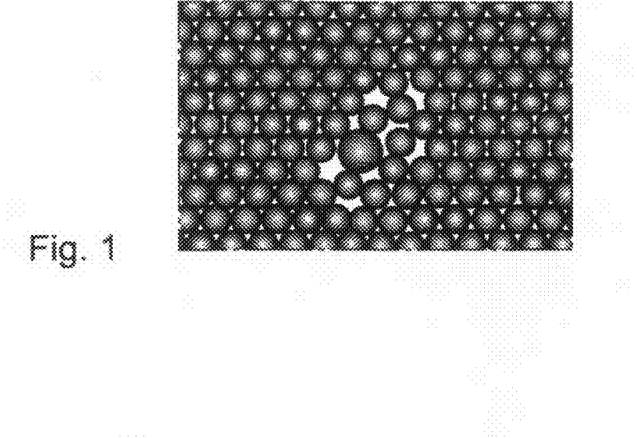
FIG. 1 shows a disturbance on a lattice of a main component caused by a solute alloy atom.

The present invention provides a possibility to predict internal mechanical properties from an electrical property, e.g. the resistivity. The general reason for the relation between electrical and mechanical properties is hidden in the crystals. Strain in the crystals structure will cause disturbances in the electron conduction bands. If, for instance, a foreign atom is dissolved in a metal, this might cause a major disturbance. This is illustrated in FIG. 1. For example, a manganese atom dissolved in aluminum causes great disorder in the surrounding aluminum mass, and thereby strains, which lead to destruction of the conduction bands of the electrons. The surroundings of the dissolved atom will become almost electrically non-conducting. Alloying elements such as iron, tin and chromium cause the same type of conditions in copper, as manganese in aluminum.

Figure 2:
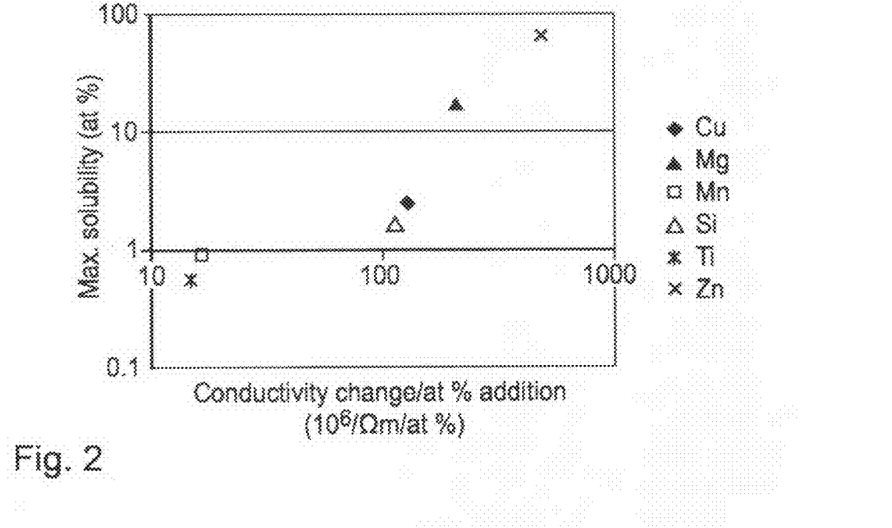
FIG. 2 shows the relation between change in conductivity and maximum solubility.

In general it can be said that the more disturbance a solute atom will cause, the more change in conductivity this specific element will cause. An element that dissolves easily within the main component, as for instance magnesium in aluminum, causes a relatively small change in conductivity, whereas an element that dissolves only with difficulty, as manganese in aluminum, causes a relatively considerable change in conductivity. So this means that the conductivity tells us something about the appearance of the diagram, as illustrated in FIG. 2.

Figure 3:
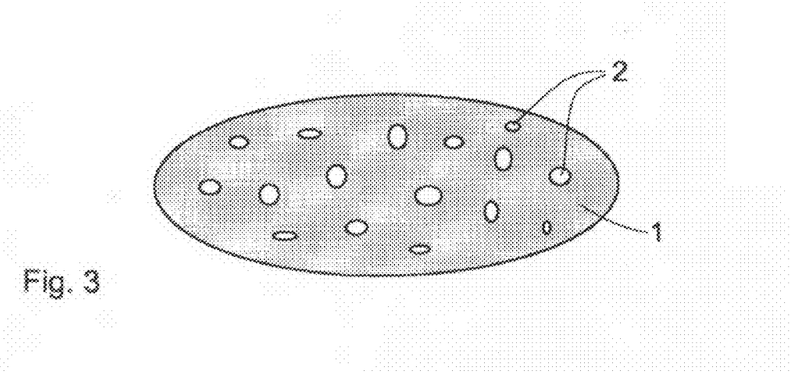
FIG. 3 shows a metal alloy object with alloying elements in main and precipitated phase.

This opens for a use of electrical conductivity as a measure of the condition inside the metal. In alloys where an alloying element is not completely soluble, the alloy can either be found in solid solution or precipitated in a separate phase. FIG. 3 shows a metal alloy object including a main phase 1 with alloying elements dissolved in a main component, and a plurality of precipitated alloy elements 2 in a precipitated phase.

Due to the present invention, using available knowledge of the thermodynamics of the alloy, the actual analysis of the object and a conductivity or resistivity measurement, the amount of dissolved and precipitated alloy can be calculated. This is an important factor when trying to predict the internal mechanical behavior of a metallic material. As this distribution is depending upon the heat treatment history it is often difficult to predict by other means.

For example, the invention could be applied on an alloy object having aluminum as main component, and manganese, silicon and magnesium as alloying elements. The mechanical behavior of aluminum is generally a strong function of the conditions in the main phase. Therefore we often will see a direct relation between mechanical properties and conductivity. Here the resistivity (=1/conductivity) is used as parameter. Mathematical models describing the mechanical behavior of different metal alloys are built based on calculated conditions in the metal, amount of dissolved alloying elements, amount and composition of precipitates. When a model has been built, it is possible to predict internal mechanical properties from resistivity measurement, chemical analysis and thickness reduction.

Figure 4:
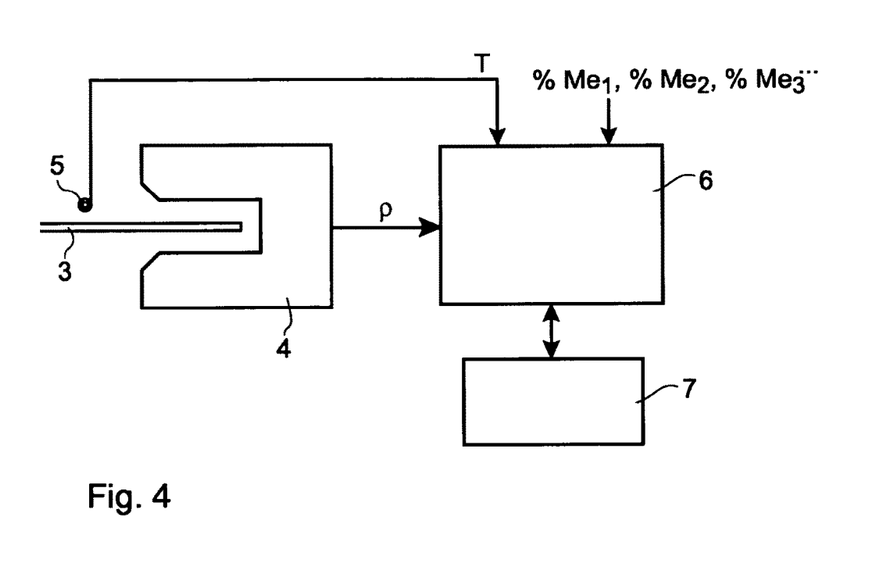
FIG. 4 shows an apparatus for estimating internal mechanical properties of a metal alloy object according to an embodiment of the invention.

FIG. 4 shows an apparatus for estimating one or more internal mechanical properties of a metal alloy object 3 according to an embodiment of the invention. The metal alloy object 3 is, for example, a metal sheet during rolling. The apparatus comprises a measuring device 4 for measuring the resistivity of the metal alloy object 3. Preferably, the measuring device 4 carries out an inductive measuring of the resistivity, for example as described in patent document U.S. Pat. No. 5,059,902. The measuring device 4 comprises coils arranged around the object 3. The coils are adapted to generate a magnetic field in the object. This magnetic field interacts with the object and causes a change in the field. The coils measure this change. The electric resistivity in the object is determined based on the measured changes in the magnetic field. This technique is called Pulsed Eddy Current (PEC). This technology makes it possible to contactlessly measure the resistivity.

A main problem when trying to measure the electrical resistivity in-line is the temperature. If the resistivity measurement is to be used for determining a property of the material, the temperature dependence of the resistivity has to be eliminated. The resistivity strongly depends on the temperature of the measured object. Accordingly, the measured resistivity has to be recalculated to a given reference temperature, for example to 20° C. For this purpose, the apparatus comprises a temperature measuring device 5 adapted to measure the temperature in the alloy object. Preferably, the temperature of the object should be measured with at least an accuracy of 1° C.

The temperature measuring device 5 is adapted to measure the temperature and the temperature gradient in the air above the object, as well as the distance to the object. With this information, and a special calibration procedure, it is possible to measure the object temperature better than 1° C. With the object temperature and the measured resistivity, the resistivity at 20° C. is calculated. Alternatively, it is also possible to use other types of temperature measuring devices, for example an infrared sensor.

The recalculation of the resistivity to the given reference temperature is made by the following expression:

$$\rho_{RT} = \rho_M - \rho_{Bas} * \alpha * (T - T_R) \quad (1)$$

where, $\rho_{RT}$=resistivity at reference temperature, $\rho_M$=measured resistivity, $\rho_{Bas}$=resistivity of the main component, $\alpha$=a constant factor describing the temperature dependence of the main component, T=the measured temperature, and $T_R$=the reference temperature.

The apparatus further comprises a computation unit 4 in which all calculations are made. The computation unit is for example a computer including processing means, such as a central processing unit (CPU), memory means for storing calculation programs and other data necessary for the calculations, and necessary input and output means. The computation unit 4 receives temperature measurements T from the temperature measuring device 5 and resistivity measurement $\rho_M$ from the resistivity measuring device 4. The computation unit 4 also receives the chemical composition of the alloy object, including the content %$Me_1$-%$Me_n$ of alloying elements in the main component. %$Me_n$ is the percentage by weight or volume, or atomic percentage of the alloying elements in relation to the whole object. n=the number of alloying elements in the alloy object. The number n of alloying elements in the object can be one or a plurality. The content of alloying elements in the alloy object is received from an analysis of the object. For each alloying element, the content typically is 1%, and accordingly the content of alloying elements is low in relation to the content of the main component.

In order to determine the internal mechanical properties of the metal alloy object, the content of dissolved alloying element has to be determined. In the following examples, the content of dissolved and precipitated alloying elements in the metal alloy object is calculated as percentage in relation to the whole alloy object. A basic problem, when trying to determine how much of an alloying element is dissolved and how much is precipitated, is that the relation between the content of dissolved and precipitated alloying element on the one hand depends on the interaction with the other alloying elements in the alloy, and on the other hand depends on the temperature. In an alloy that consists of many alloying elements, for example 5-10, the conditions become very complicated. All alloying elements interact more or less with each other and affect the degree of solubility. However, even for alloys consisting of many alloying elements, it is possible to calculate the degree of solubility in dependence on the temperature by means of thermodynamic calculations. There are commercially available programs for such calculations, for example Termo-Calc™.

A thermodynamic computation unit is implemented in the computation unit 4. From thermodynamic calculations a plurality of equations of the following type is provided:

$$\%Me_1 = C_1 * \text{Exp}(D_1/T_{eq})$$

$$\%Me_2 = C_2 * \text{Exp}(D_2/T_{eq})$$

$$\%Me_3 = C_3 * \text{Exp}(D_3/T_{eq})$$

$$\%Me_n = C_4 * \text{Exp}(D_4/T_{eq}) \quad (2)$$

Where,
$\%Me_n$=the content of dissolved alloying element n in the alloy object, calculated in relation to the whole object.
$T_{eq}$=an equilibrium temperature,
$C_n$, $D_n$=constants that depend on the actual composition of the alloy object. The constants $C_n$ and $D_n$ are calculated for each alloying element by means of thermodynamic calculations.

Alternatively, it is possible to formulate it as if $C_n$ and $D_n$ are functions of the chemical composition of the alloy object:

$$\%Me_1 = Fu1(\%Me_1 - \%Me_n, T_{eq})$$

$$\%Me_2 = Fu2((\%Me_1 - \%Me_n, T_{eq})$$

$$\%Me_3 = Fu3((\%Me_1 - \%Me_n, T_{eq})$$

$$\%Me_n = Fu4((\%Me_1 - \%Me_n, T_{eq}) \quad (3)$$

It is also possible to calculate the content of precipitated alloying elements in the alloy, as the composition of the precipitations is known from the thermodynamic computations, and since we know the total content of each alloying element in the alloy. The content $\%Me_{np}$ of precipitated alloying element n in the alloy object is calculated by the following expression:

$$\%Me_{np} = \%Me_n - \%Me_n \quad (4)$$

$\%Me_n$=the total content of the alloying element n in the metal alloy object.
$\%Me_n$=the content of dissolved alloying element n in the metal alloy object.
$\%Me_{np}$=the content of precipitated alloying element n in the metal alloy object.

The expressions 2 and 3 make it possible to calculate the percentage of dissolved alloying elements in the alloy object at different equilibrium temperatures $T_{eq}$. A problem is then that this equilibrium temperature $T_{eq}$ is ambiguous. When the temperature is high, about 500 degrees, the speed of the processes in the material is so high that the processes are almost always in equilibrium. In the contrary case, at room temperature the processes in the material are so slow that there is rarely equilibrium in the processes. If a metal alloy sheet is quickly cooled from 500° C. to room temperature, the solubility that existed at 500° C. will be preserved in the material (a supersaturated solution). But if the sheet is cooled slowly, the solubility will be decreased. This means that an object observed at room temperature appears to have different equilibrium temperatures in dependence on which cooling rate it has gone through.

The following expression relates the resistivity $\rho_{RT}$ at the reference temperature, to the content $\%Me_n$ of dissolved alloying elements:

$$\rho_{RT} = \rho_{Bas} + E_1 * \%Me_1 + E_2 * \%Me_2 + \ldots + E_n * \%Me_n \quad (5)$$

$\rho_{Bas}$ is the resistivity of the main component.
$E_n$ are constants, denoted the resistivity constant, that reflect the strength of the influence of the alloying elements on the resistivity. The constants $E_n$ are known, for example, from published tables. For example, the resistivity constant for zinc is 2.1 nΩm/at % and the resistivity constant for magnesium is 60 nΩm/at %.

Mostly the content of precipitations is low, which means that the resistivity of the main component is the same as for the total alloy. If the content of precipitations is so large that they will influence the calculations, the average resistivity for a unit tube is calculated based on the resistivity of the main component, the percentage by volume of the precipitations, and the resistivity. Generally, the precipitations are bad conductors in relation to the main component, so they can be considered to be non-conducting. The total volume $Vol_{TOT}$ of the precipitations can then be added and computed as non-conducting. We can then use the expression:

$$\rho_{RT} = \rho_{Bas}/(1 - Vol_{TOT}) \quad (6)$$

By means of the expressions 2 or 3 and 5 or 6, the thermodynamic calculations of the coefficients $C_n$, $D_n$, and the measured resistivity, it is now possible to determine the equilibrium temperature $T_{EQ}$ appearing. The expressions 2 or 3 and 5 or 6 are calculated iteratively by guessing a suitable value of the equilibrium temperature $T_{EQ}$. The calculated resistivity is compared with the measured resistivity, which has been compensated for the temperature. The iterative calculation continuous until the calculated resistivity corresponds to the measured resistivity. Thereby, a real value of the equilibrium temperature is obtained. By means of the calculated equilibrium temperature, the known contents of the alloying elements in the alloy object and again thermodynamic computations, the content of dissolved alloying elements and precipitations are determined.

The strength of an alloy object is reflected by the following internal mechanical properties: the tensile strength, the yield strength and the elongation of the object. The strength of an alloy object is mainly dependent on the degree of cold working, i.e. the reduction during the cold working, and the content of dissolved alloying elements.

The computation unit also comprises means for executing mechanical computations for calculation of one or more internal mechanical properties of the metal alloy object. The mechanical calculations are based on a mechanical model of the metal alloy of the object. The mechanical model is, for example, of the following type:

$$\text{Strength} = \text{Strength of the main component} + A * Hu(\epsilon) + (F_1 * \%Me_1 + F_2 * \%Me_2 + F_3 * \%Me_3 + \ldots) + (G_A Vol_A + G_B Vol_B + \ldots) \quad (7)$$

$$\epsilon = \ln(A_0/A_F) \quad (8)$$

The strength can either be the tensile strength, the yield strength, or the elongation. The strength of the main component is the tensile strength, the yield strength, or the elongation of the main component.

$A$=a constant which depends on the alloy and can be calculated based on the knowledge of the composition of the alloy.

$Hu(\epsilon)$=a function of the degree of reduction $\epsilon$ of the object during cold working of the object, and is defined as the expression 8, where $A_0$=the cross section area before the deformation.

$A_F$ is the cross section area after the deformation.

$A^*Hu(\epsilon)$ is normally described by a simple power function of $\epsilon$ and is known for common metals such as aluminum.

$F_1$, $F_2$, $F_3$=constants describing how the different alloying elements in the main phase influence the strength, and is to some degree possible to be found in known literature.

%$Me_1$, %$Me_2$, %$Me_3$=the calculated content of dissolved alloying elements.

The last part of the expression 7, $(G_A Vol_A + G_B Vol_B + \ldots)$ describes how the precipitations influence the strength. The constants $G_A$, $G_B$ describe the influence from different precipitations and VolA, VolB are the volume portions of the different precipitations calculated above. The last part of the computation can often be disregarded, but is necessary if the computations have to be exact. In dependence on whether the yield strength or the tensile strength is to be determined, different values of the constants $G_A$, $G_B$ are used.

The following equation can be used to calculate the tensile strength $\sigma_{tensile}$:

$$\sigma_{tensile} = \sigma_{tensile\ main\ component} + At^*Hu(\epsilon) + (Ft_1^* \%Me_1 + Ft_2^* \%Me_2 + Ft_3^* \%Me_3 + \ldots) + (Gt_A Vol_A + Gt_B Vol_B + \ldots) \quad (9)$$

Where At, $Ft_n$ and $Gt_N$ are a setup of constants valid for tensile strength calculation, and $\sigma_{tensile\ main\ component}$ is the tensile strength of the main component in the alloy.

The following equation can be used to calculate the yield strength $\sigma$ yield:

$$\sigma_{yield} = \sigma_{yield\ main\ component} + Ay^*Hu(\epsilon) + (Fy_1^* \%Me_1 + Fyt_2^* \%Me_2 + Fy_3^* \%Me_3 + \ldots) + (Gy_A Vol_A + Gy_B Vol_B + \ldots) \quad (10)$$

Where Ay, $Fy_n$ and $Gy_N$ are a setup of constants valid for yield strength calculation, and $\sigma_{yield\ main\ component}$ is the yield strength of the main component in the alloy.

The strength calculated according to expression 7, 9 or 10 could be the tensile strength or the yield strength, with values on constants $F_n$ and $G_N$ different for tensile strength calculation and yield strength calculation. The values of those constants can sometimes be found in the literature, but when not it is advisable to make laboratory tests where samples with different contents of dissolved alloying elements and with different contents of precipitations are investigated in relation to tensile strength or yield strength measured with standard technique. From such tests the values of constants can be determined for different degree of deformation.

In some instances, for instance when very high accuracy is needed in determination of strength, the simple, linear, form of expression 7 is not precise enough. More complicated relations between the parameters used in expression 7 then need to be formulated. Still it is generally valid that the strength will be a function of the strength of the main component, the dissolved alloying elements in the main component and the amount and properties of the precipitates. And still it is generally valid that the amount of precipitates can be calculated as the difference between total alloy content and dissolved alloy in the main component, as in expression 4, once the type of precipitates have been determined, for instance from thermodynamic calculation.

The apparatus shown in FIG. 4 also comprises an operator panel 5. The computed internal mechanical properties are transferred from the computation unit 4 to the operator's panel 5 and for example displayed on a display device of the panel.

The calculated mechanical properties can, for example, be used for determining the temperature and time for a heat treatment of an object during production thereof. For example, heat treatment of a metal alloy sheet during production of the sheet. Today, the time and temperature for the heat treatment are calculated based on the degree of reduction of the sheet during rolling, the type of material and a desired strength. If this calculation also is based on a calculated strength, according to the method described above, the spread in the strength after the heat treatment could be considerably reduced. This means that the resistivity of the sheet has to be measured during the rolling process and the final strength has to be calculated for different heat treatments.

Figure 5:
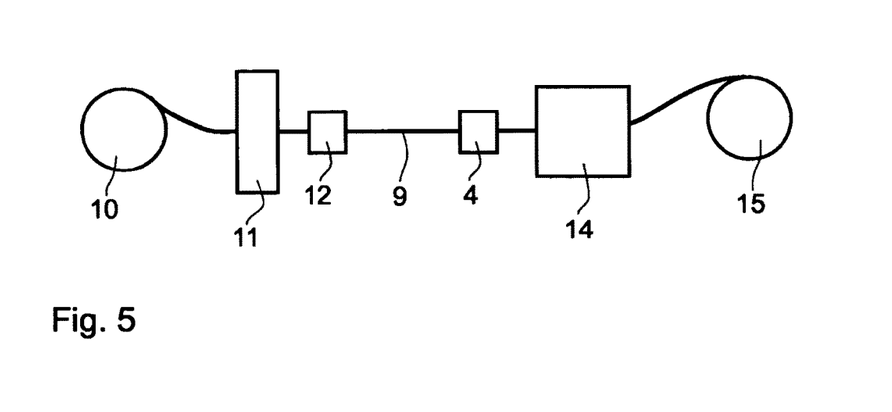
FIG. 5 shows a stretching machine for producing an alloy strip.

FIG. 5 shows a tension leveling machine for producing an alloy strip 9. The machine comprises an incoming coil 10, a leveling machine 11, a heater 12, which for example inductively heats the strip 9, a resistivity measuring device 4, an alignment device 14, and an outgoing coil 15. The implementation of the invention in a stretching machine makes it possible to soften strips, which tend to be too stiff. Preferably, the strips are made stiffer than desired from the beginning, and the strips are later softened by means of heat treatment in the heater 12. The estimated strength is then used to estimate how much softening is necessary, in order to achieve the desired stiffness of the material. The temperature needed for the softening is rather low, for example 250° C. should be well enough. With this kind of heat treatment it is possible to essentially increase the accuracy of the strength for produced strips.

Figure 6:
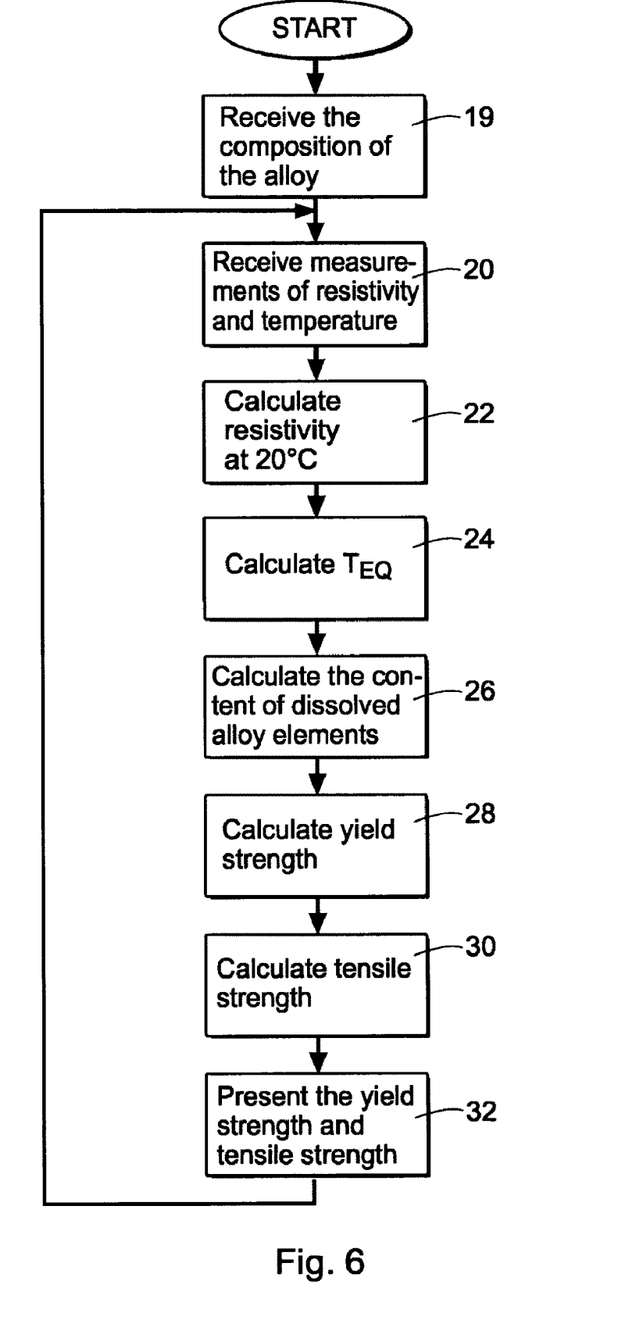
FIG. 6 shows a method for estimating internal mechanical properties of a metal alloy object according to an embodiment of the invention.

FIG. 6 is a flow diagram illustrating a method and a computer program product according to an embodiment of the present invention. It is to be understood that each block of the flow diagram can be implemented by computer program instructions run on one or more computers.

Before the calculation begins the chemical composition %$Me_1$, %$Me_2$, ... %$Me_n$ of the metal alloy object is received and stored, block 19. Measurements of the resistivity $\rho_M$ and temperature T of the object are continuously received from the production process, block 20. The resistivity is recalculated to the reference temperature $T_R$, in this case to 20° C., according to formula 1, block 22.

The equilibrium temperature $T_{EQ}$ is calculated by means of the expressions 2 or 3 and 5, based on the measured resistivity $\rho_{RT}$ and the stored chemical composition %$Me_1$, %$Me_2$, ... %$Me_n$ of the metal alloy object, block 24. Thereafter, for each alloying element in the object, the content %$Me_n$ of the dissolved alloying element in the alloy object is calculated by means of the expression 2 or 3, based on the calculated equilibrium temperature $T_{EQ}$, block 26.

The yield strength $\sigma_{yield}$ is calculated according to the expression 10 based on the calculated content %$Me_1$, %$Me_2$, ... %$Me_n$ of the dissolved alloying elements and the stored composition %$Me_1$, %$Me_2$, ... %$Me_n$ of the alloy object, block 28. The tensile strength $\sigma_{tensile}$ is calculated by means of the expression 9 based on the calculated content %$Me_1$, %$Me_2$, ... %$Me_n$ of the dissolved alloying elements and the stored chemical composition %$Me_1$, %$Me_2$, ... %$Me_n$ of the alloy object, block 30. The calculated yield strength and tensile strength are presented to the operator, block 32. In an alternative embodiment, the yield strength and tensile strength are used as a base for further calculations to be used for controlling the production of the object, in order to improve the quality of the produced object.

In order to supervise a production process for producing a metal alloy object the ratio R between the content of dissolved alloying element n and the content of precipitated alloying element n in the metal alloy object is calculated and presented to an operator.

$$R_n = \%Me_n / \%Me_{np} \tag{11}$$

Alternatively, the sum of the ratio for all alloying elements in the object is calculated and used for the supervision of the production process.

The present invention makes it possible to predict internal mechanical properties from resistivity measurements or conductivity measurements, analysis of the chemical composition, and the degree of reduction. And here we have been able to calculate the amount of dissolved and precipitated elements, using the analysis, and thermodynamic calculation.

The term comprises/comprising when used in this specification is taken to specify the presence of stated features, integers, steps or components. However, the term does not preclude the presence or addition of one or more additional features, integers, steps or components or groups thereof.

The invention claimed is:

1. A method of estimating one or more internal mechanical properties of a metal alloy object with a known chemical composition based on a resistivity of the metal alloy object, the method comprising:
   determining the resistivity of the metal alloy object,
   calculating a content of dissolved alloying elements in the metal alloy object based on the determined resistivity and the chemical composition of the metal alloy object, and based thereon,
   calculating at least one internal mechanical property of the metal alloy object,
   receiving a temperature of the metal alloy object,
   calculating the resistivity at a reference temperature based on the temperature of the object and the measured resistivity, and
   calculating the content of dissolved alloying elements in the metal alloy based on the resistivity at the reference temperature.

2. The method according to claim 1, wherein the resistivity of the alloy object is continuously, or at least repeatedly measured during production of the object and said internal mechanical property of the object is repeatedly calculated based thereon.

3. The method according to claim 1, wherein the metal alloy object undergoes a certain degree of thickness reduction during production of the object, and said mechanical property of the metal alloy object is calculated based on the degree of thickness reduction.

4. The method according to claim 1, wherein the reference temperature is in the interval of 15-30° C.

5. The method according to claim 1, wherein the content of dissolved alloying elements in the metal alloy object is calculated utilizing thermodynamic calculations.

6. The method according to claim 1, wherein the content of dissolved alloying elements in the metal alloy is calculated based on a first mathematical relationship between the resistivity in the metal alloy and the content of dissolved alloying elements in the metal alloy and the known chemical composition of the metal alloy.

7. The method according to claim 1, wherein the main component of said alloy is aluminum.

8. The method according to claim 1, wherein the resistivity of the metal alloy object is measured by utilizing a contactless measuring method.

9. The method according to claim 1, further comprising:
   calculating the content of precipitated alloying elements in the metal alloy object, and based thereon
   calculating said at least one internal mechanical property of the metal alloy object.

10. The method according to claim 1, further comprising:
    supervising the quality of the produced object based on the calculated internal mechanical property of the object.

11. The method according to claim 1, wherein said internal mechanical property of the object is continuously or at least repeatedly calculated during production of the object, the method further comprising:
    continuously or at least repeatedly adjusting the production process in accordance with the estimated property of the object in order to improve the quality of the produced object.

12. The method according to claim 1, wherein said internal mechanical property of the object is continuously or at least repeatedly calculated during production of the object, the method further comprising:
    calculating a degree of heating of the alloy object based on the calculated mechanical property, and heat treating the alloy object in accordance with the calculated degree of heating.

13. The method according to claim 1, further comprising:
    comparing the calculated value of the internal mechanical property of the alloy object with a value of the same internal mechanical property measured on a sample of the same metal alloy object in a mechanical test, and adjusting the calculated value in accordance with the measured value.

14. The method according to claim 1, further comprising:
    supervising a quality of a moving alloy object during production of the object.

15. The method according to claim 1, further comprising:
    controlling a production process for producing metal alloy objects, in accordance with the estimated internal mechanical property in order to improve the quality of the produced objects.

16. The method according to claim 1, further comprising:
    estimating a strength of an aluminum alloy sheet or strip during production of the sheet or strip.

17. The method according to claim 1, wherein the content of dissolved alloying elements in the metal alloy is calculated based on a second mathematical relationship between the content of a dissolved alloying element in the metal alloy and the known chemical composition of the metal alloy and an equilibrium temperature.

18. The method according to claim 8, wherein the equilibrium temperature is iteratively calculated based on said first and second mathematical relationship, and the content of dissolved alloying elements in the metal alloy is calculated based on the calculated equilibrium temperature and said second mathematical relationship.

19. The method according to claim 1, wherein said internal mechanical property reflects the strength of the metal alloy object.

20. The method according to claim 19, wherein said internal mechanical strength property is calculated based on the calculated content of dissolved alloying elements in the metal alloy and a known strength property of the main component of the alloy.

21. The method according to claim 1, wherein said mechanical property is the tensile strength.

22. The method according to claim 21, wherein the tensile strength of the metal alloy object is calculated based on the content of dissolved alloying elements in the metal alloy, the known chemical composition of the metal alloy, and a known tensile strength of the main component of the alloy.

23. The method according to claim 1, wherein said mechanical property is the yield strength.

24. The method according to claim 23, wherein the yield strength of the metal alloy object is calculated based on the content of dissolved alloying elements in the metal alloy, the known chemical composition of the metal alloy, and a known yield strength for the main component of the alloy.

25. An apparatus for estimating one or more internal mechanical properties of a metal alloy object with a known chemical composition based on the resistivity of the metal alloy object, the apparatus comprising:
  a device for measuring the resistivity of the metal alloy object, and
  a computation unit configured to calculate the content of dissolved alloying elements in the metal alloy object based on the measured resistivity and the known chemical composition of the metal alloy, and based thereon to calculate at least one internal mechanical property of the metal alloy object, receiving a temperature of the metal alloy object, calculating the resistivity at a reference temperature based on the temperature of the object and the measured resistivity, and calculating the content of dissolved alloying elements in the metal alloy based on the resistivity at the reference temperature.

26. The apparatus according to claim 25, wherein said computation unit is adapted to calculate the content of dissolved alloying elements in the metal alloy object with thermodynamic calculations.

27. The apparatus according to claim 25, wherein said internal mechanical property reflects the strength of the metal alloy object.

28. The apparatus according to claim 25, further comprising:
  a temperature measuring device for measuring the temperature in the metal alloy object during production of the object, wherein said computation unit is adapted to calculate the resistivity at a given reference temperature based on the measured temperature and the measured resistivity.

29. The apparatus according to claim 25, wherein the reference temperature is in the interval of 15-30° C.

30. The apparatus according to claim 25, wherein said measuring device is designed to contactlessly measure the resistivity of the metal alloy object.

31. The apparatus according to claim 30, wherein said measuring device is designed to measure the resistivity of the metal alloy object by eddy current measurements.

* * * * *

UNITED STATES PATENT AND TRADEMARK OFFICE
CERTIFICATE OF CORRECTION

PATENT NO. : 8,263,409 B2
APPLICATION NO. : 12/084973
DATED : September 11, 2012
INVENTOR(S) : Sten Linder et al.

It is certified that error appears in the above-identified patent and that said Letters Patent is hereby corrected as shown below:

Col. 16, line 8-15, Claim 28 should read as follows

28. The apparatus according to claim 25, further comprising:
a temperature measuring device for measuring the temperature in the metal alloy object during production of the object, wherein said computation unit is ~~adapted~~ configured to calculate the resistivity at a given reference temperature based on the measured temperature and the measured resistivity.

Signed and Sealed this
Twenty-ninth Day of January, 2013

David J. Kappos
*Director of the United States Patent and Trademark Office*